United States Patent
Sharma et al.

(10) Patent No.: US 6,838,569 B2
(45) Date of Patent: Jan. 4, 2005

(54) PROCESS FOR PREPARATION OF PACLITAXEL TRIHYDRATE AND DOCETAXEL TRIHYDRATE

(75) Inventors: Arun Prakash Sharma, Nadia (IN); Subrata Sarkar, Nadia (IN); Jyan Shanker Mahanty, Nadia (IN)

(73) Assignee: Dabur India Limited, West Bengal (IN)

(*) Notice: Subject to any disclaimer, the term of this patent is extended or adjusted under 35 U.S.C. 154(b) by 0 days.

(21) Appl. No.: 10/419,782

(22) Filed: Apr. 22, 2003

(65) Prior Publication Data

US 2004/0116720 A1 Jun. 17, 2004

(30) Foreign Application Priority Data

Dec. 16, 2002 (IN) ........................................ 697/CAL/02

(51) Int. Cl.⁷ ............................................ C07D 305/14
(52) U.S. Cl. ...................................................... 549/510
(58) Field of Search .......................................... 549/510

(56) References Cited

U.S. PATENT DOCUMENTS

| | | | |
|---|---|---|---|
| 5,476,954 A | 12/1995 | Bourzat et al. | |
| 5,616,739 A | 4/1997 | Mas et al. | |
| 5,637,723 A | 6/1997 | Commercon et al. | |
| 6,002,022 A | 12/1999 | Authelin et al. | |
| 6,022,985 A | 2/2000 | Authelin et al. | |
| 6,197,980 B1 | 3/2001 | Durand et al. | |
| 6,506,905 B1 | 1/2003 | Prakash et al. | |

OTHER PUBLICATIONS

U.S. Appl. No. 10/431,499, Sharma et al., filed Aug. 5, 2003.

U.S. Appl. No. 10/213,431, Sharma et al., filed Aug. 7, 2002.

Wani et al., J. Am. Chem. Soc., vol. 93, pps. 2325–2326 (1971).

*Primary Examiner*—Taofiq Solola
(74) *Attorney, Agent, or Firm*—Marina V. Schneller; Venable LLP

(57) ABSTRACT

A process for converting paclitaxel or docetaxel to the respective trihydrate characterized by very high purity, comprises dissolving either paclitaxel or docetaxel in a mixture of alkane and chlorinated alkane to provide a crude product of 65–75% assay and dissolving the crude product in an alkyl ketone, followed by addition of an alkane to provide a product of increased chromatographic purity; dissolving the product of increased chromatographic purity in an aliphatic nitrile, with addition of water to precipitate taxane trihydrate.

11 Claims, No Drawings

PROCESS FOR PREPARATION OF PACLITAXEL TRIHYDRATE AND DOCETAXEL TRIHYDRATE

BACKGROUND OF THE INVENTION

Purification of semi-synthetic paclitaxel and docetaxel, which are well known and approved chemotherapeutic drugs for treatment of metastatic cancer, is a challenging problem due to formation of a number of degradation products along the synthetic route. Furthermore, purified taxanes are found to undergo degradation, even under controlled storage condition. Therefore, it becomes desirable to develop stable crystalline forms of these molecules, which retain the desirable anti-cancer properties. Towards this end Rhone-Poulenc Rover, S.A., France has developed processes for preparation of trihydrates of paclitaxel and docetaxel. According to Authelin et al, U.S. Pat. No. 6,022,985 stability studies have shown that docetaxel trihydrate is stable at 4° C., 25° C., and 35° C. in an atmosphere with 90% relative humidity upto 18 months without modification in its crystalline form. Under similar condition, anhydrous docetaxel slowly changes its crystalline form to the trihydrate form. This U.S. Patent describes a process for the preparation of docetaxel trihydrate by crystallization of anhydrous docetaxel from a mixture of water and an aliphatic alcohol containing 1–3 carbon atom, specifically ethanol. The water/alcohol weight ratio used in this innovation is about 2/1. The crystals obtained thus, are dried under defined condition of temperature (about 40° C.), pressure (4–7) kPa and relative humidity of about 80%. The crystallization was also performed in the presence of ascorbic acid.

In U.S. Pat. No. 6,197,980 to Durand et al., a process for centrifugal partition chromatography of crude docetaxel in two partially miscible phases using an aliphatic hydrocarbon, an ester, an alcohol and water, is described. Docetaxel trihydrate is obtained by concentrating the column fractions. The process did not specify drying conditions.

Similarly paclitaxel trihydrate is reported to have markedly superior stability in comparison to the anhydrous product. (Authelin el al U.S. Pat. No. 6,002,022). According to this invention, paclitaxel trihydrate is obtained from a mixture of water and an aliphatic alcohol containing upto three carbon atoms, specifically methanol. The water/alcohol weight ratio used in this process is between 3/1 to 1/3. The crystals, thus obtained, are dried at about 40° C. under reduced pressure.

Both the U.S. Pat. Nos. 6.022,985 and 6,002.022 are limited in scope, in terms of solvents that could be used for crystallization. Both use aliphatic alcohols containing 1–3 carbon atoms as the solvent of choice. In addition, paclitaxel or docetaxel used for crystallization has to be chromatographed beforehand. Furthermore, the drying conditions used in these patents are specific and recommended conditions are not easy to maintain. In view of the above we have developed a process, for preparation of paclitaxel trihydrate and docetaxel trihydrate, which do not require chromatography. Instead, we use solvent—based purification technique, which is faster, cheaper, and can be scaled up easily. We also found that the choice of solvents in the crystallization of paclitaxel or docetaxel is not necessarily limited to alcohols and aliphatic nitriles are as effective as alcohols.

Objects of the Invention

An object of the invention is to provide a process for obtaining pharmaceutical grade docetaxel trihydrate and paclitaxel trihydrate from semi-synthetic crude docetaxel or paclitaxel.

Another object of this invention is to propose a process which produces paclitaxel trihydrate and docetaxel trihydrate of chromatographic purity>99.5%.

Still another object of the present invention is to propose a simple process, of the preparation of paclitaxel trihydrate and docetaxel trihydrate.

SUMMARY OF THE INVENTION

According to this invention there is provided a process for the preparation of paclitaxel trihydrate and doctaxel trihydrate comprising: (a) treating taxane selected from paclitaxel and docetaxel with a mixture of alkane and chlorinated alkane to obtain a crude product of 65–75% assay; (b) dissolving the crude product thus obtained in alkyl ketone followed by slow addition of an alkane to increase chromatographic purity, (c) dissolving the taxane of step (b) in an aliphatic nitrile at a temperature of 50–70° C., (d) adding purified water to the product of step (c) to precipitate taxane trihydrate; and (e) filtering and drying the product of step (d) to obtain taxane trihydrate of C.P.>99.5% and 98–102% assay.

DETAILED DESCRIPTION OF THE INVENTION

In accordance with the present invention there is provided a process for preparing paclitaxel trihydrate and docetaxel trihydrate. The procedure comprises the following steps:

Step 1

Crude taxane (C.P. 60–70%; assay 40–55%) is added to mixture of chlorinated alkane and alkane (1:9; 10 times with respect to taxane). The mixture is stirred for 2–6 h, preferably 4h at 25–30° C. and then filtered under vacuum to obtain a material of 55–65% assay. Step 1 is repeated to increase the purity of the crude product to 65–75% assay. The preferred chlorinated alkane is dichloromethane and the preferred alkane is hexane.

Step 2

The taxane obtained in step 1 is dissolved in alkyl ketone (6–20 times with respect to crude weight) at 20–45° C. The solution is cooled, filtered and then an alkane (2–3 times with respect to alkyl ketone) is added slowly under stirring at 25–35° C. The mixture is stirred further at 25–35° C. for 2–4 h, filtered and the residue is dried under vacuum. In case of repetition of step 2 the ratio of alkyl ketone and alkane used with respect to taxane is 20–30 times and 40–60 times respectively After step 2 chromatographic purity of taxane reaches 93–99.7%. The preferred alkyl ketone is a lower alkyl ketone, most preferably acetone Among alkanes used, hexane is most preferable.

Step 3

The taxane obtained in step 2 is dissolved in an aliphatic nitrite, most preferably acetonitrile (20–30 times with respect to taxane) at 50–70° C. To this solution, purified water (2–3 times with respect to aliphatic nitrile) is added slowly and then the mixture is stirred further at 10–25° C. for 2–4 h. The precipitated material is filtered and then dried at 35–45° C. under 650–700 mm mercury vacuum for 36–40 h with powdering at regular interval under relative humidity 80–90%. The taxane thus obtained, his C.P.>99.5%, assay 98–102% and water content 6.2–7.2%.

The invention will now be explained in detail with the help of the following non-limiting examples.

EXAMPLE 1

Paclitaxel

Step 1 (Alkane—Chlorinated Alkane Purification)

Crude paclitaxel (1.0 Kg, w/w purity 52%, chromatographic purity 67%) is added to mixture of dichloromethane—hexane (1:9; 10L) under stirring. Stirring is continued at 25–30° C. for 4 h. The solid thus obtained is filtered and then dried under reduced pressure to obtain paclitaxel (assay 64.8%). Step 1 is repeated again to obtain paclitaxel (650 gm: assay 75%; C.P. 82.4%)

Step 1 (Acetone—Hexane Purification)

a) Paclitaxel (650 gm, from step 1) is dissolved in acetone (6.5 L) at 40° C. under stirring. The solution is cooled at 30° C. and then it is filtered. To this solution hexane (19.5 L) is added under stirring at 30° C. The mixture is further stirred at 25–30° C. for 3 h, filtered and the residue is dried under reduced pressure at 50–55° C. for 8 h to obtain paclitaxel (520 gm, C.P. 96.5%).

b) Paclitaxel (520 gm, from step 2a) is dissolved in filtered acetone (15.6 L) at 45° C. under stirring and then cooled to 25° C. To this solution, filtered hexane (31.2L) is added under stirring. The mixture is stirred for 2h at 25–30° and then filtered. The residue is dried under condition as described under step 2a to obtain paclitaxel (440 gm, C.P. 99.57%).

Step 3 (Crystallisation from Acetonitrile—Water)

Paclitaxel (440 gm obtained from step 2b) is dissolved in filtered acetonitrile (13.2 L) at 65° C. under stirring. To this solution purified water (39.6 L) is added slowly and then the mixture is stirred further at 15–20° C. for 3 h. The precipitated material is filtered and then dried at 36° C. under 650 mm mercury vacuum for 36h to obtain paclitaxel trihydrate (410 gm, C.P. 99.55%, assay 99.6% on dry basis, water content 6.4%).

EXAMPLE II

Docelaxel

Step 1 (Alkane—Chlorinated Alkane Purification)

Crude dovetaxel (1.0 KG, w/w purity 55%., chromatographic purity 70%) is added to mixture of dichloromethane—hexane (1:9; 10 L) under stirring. Stirring is continued at 25–30° C. for 4 h. The solid thus obtained is filtered and then dried under reduced pressure to obtain docetaxel (assay 63.5%). Step 1 is repeated to obtain docetaxel (670 gm; assay 74%; C.P. 81.6%).

Step 2 (Acetone—Hexane Purification)

a) docetaxel (670 gm, from step 1) is dissolved in acetone (6.7 L) at 40° C. under stirring. The solution is cooled to 25° C. and then it is filtered. To this solution bexane (15.4 L) is added under stirring. The mixture is further stirred at 25–30° C. for 3 h, filtered and the residue is dried under reduced pressure at 50–55° C. for 8 h to obtain docetaxel (510 gm, C.P. 97%).

b) Docetaxel (510 gm, from step 2a) is dissolved in filtered acetone (15.3 L) at 40° C. under stirring and then cooled to 25° C. To this solution, for 2h and then filtered under vacuum. The residue is dried under condition as described under step 2a to obtain docetaxel (460 gm, C.P. 99.53%).

Step 3 (Crystallisation from Acetonitrile—Water)

Docetaxel (460 gm obtained from step 2b) is dissolved in filtered acetonitrile (13.8 L) at 68° C. under stirring. To this solution purified water (41.4 L) is added slowly and then the mixture is stirred further at 15–20° C. for 3h. The precipitated material is filtered and then dried at 36° C. under 650 mm mercury vacuum for 36h to obtain docetaxel trihydrate (415 gm, C.P. 99.59%, assay 99.2% on dry basis, water content 6.8%).

What is claimed is:

1. A process for the purification of paclitaxel trihydrate and docetaxel trihydrate comprising:
   (a) treating at least one crude taxane selected from the group consisting of paclitaxel and docetaxel of chromatographic assay of 40–55% with a mixture of dichloromethane and hexane to obtain a product;
   (b) dissolving the product obtained in (a) in acetone followed by addition of hexane to increase chromatographic purity and provide a product of step (b);
   (c) dissolving the product of step (b) in acetonitrile at a temperature of 50–70° C.;
   (d) adding purified water to a product of step (c) to precipitate the taxane; and
   (e) filtering and drying a product of step (d) to obtain at least one taxane trihydrate selected from the group consisting of paclitaxel trihydrate and docetaxel trihydrate.

2. The process as claimed in claim 1, which comprises adding crude taxane selected from the group consisting of paclitaxel and docetaxel of chromatographic assay of 40–55% to a 1:9 mixture of dichloromethane and hexane; subsequently stirring at 25–30° C.; filter and drying a residue at 50–55° C. under reduced pressure.

3. The process as claimed in claim 1, which further comprises repeating step (a) to increase chromatographic assay of crude paclitaxel and docetaxel to 65–75%.

4. The process as claimed in claim 1, which comprises dissolving paclitaxel and docetaxel of step (a) in acetone at 25–45° C. to form a solution; cooling the solution and filtering; and adding hexane at 25–35° C. and stirring for 2 to 4 hours and filtering; isolating a residue and drying it under reduced pressure at 50–55° C.

5. The process as claimed in claim 1, which further comprises repeating step (b) to increase chromatographic purity to 93–99.7%.

6. The process as claimed in claim 4, wherein the ratio of acetone/taxane is 6–20 and the ratio of hexane/acetone is 2–3.

7. The process claimed in claim 5, wherein the ratio of acetone/taxane is 20 to 30 and the ratio of hexane/acetone is 2 to 3 and the ratio of hexane/acetone is 2 to 3.

8. The process as claimed in claim 1, wherein a ratio of acetonitrile to paclitaxel and docetaxel of step (b) is 20–30 and dissolving is conducted at 50 to 70° C.

9. The process as claimed in claim 1, wherein a water: acetonitrile ratio in step (d) is 2–3.

10. The process as claimed in claim 1, wherein the water containing mixture of step (d) is stirred at 10–25° C. for 2–4 hours.

11. The process claimed in claim 1, wherein a water containing mixture of step(d) is stirred at 10–25° C. for 2–4 hours and wherein the product obtained from step (d) is dried at 35–45° C. under 650–700 mm mercury vacuum for 36–40 hours with powdering under relative humidity of 80–90% to obtain said paclitaxel trihydrate and docetaxel trihydrate.

* * * * *